(12) United States Patent
Dale et al.

(10) Patent No.: US 7,070,967 B2
(45) Date of Patent: Jul. 4, 2006

(54) HIGH SPEED, CONSECUTIVE BATCH OR CONTINUOUS, LOW EFFLUENT PROCESS FOR THE PRODUCTION OF ETHANOL FROM MOLASSES, STARCHES, OR SUGARS

(75) Inventors: M. Clark Dale, W. Lafayette, IN (US); Mark Moelhman, Lafayette, IN (US)

(73) Assignee: Bio-Process Innovation, Inc., West Lafayette, IN (US)

( * ) Notice: Subject to any disclaimer, the term of this patent is extended or adjusted under 35 U.S.C. 154(b) by 0 days.

(21) Appl. No.: 10/921,182

(22) Filed: Aug. 19, 2004

(65) Prior Publication Data

US 2005/0019932 A1 Jan. 27, 2005

Related U.S. Application Data

(63) Continuation of application No. 10/056,063, filed on Jan. 28, 2002, now Pat. No. 6,861,248.

(60) Provisional application No. 60/264,070, filed on Jan. 26, 2001.

(51) Int. Cl.
- *C12N 1/18* (2006.01)
- *C12N 15/74* (2006.01)
- *C12P 7/06* (2006.01)
- *C12P 7/08* (2006.01)

(52) U.S. Cl. ............ 435/163; 435/161; 435/254.1; 435/255.2; 435/483

(58) Field of Classification Search ........... 435/161, 435/163, 254.1, 255.2
See application file for complete search history.

(56) References Cited

U.S. PATENT DOCUMENTS

| | | | | |
|---|---|---|---|---|
| 4,560,659 A | * | 12/1985 | Asturias | 435/162 |
| 5,693,526 A | * | 12/1997 | Mondal et al. | 435/225.2 |
| 6,379,964 B1 | * | 4/2002 | del Cardayre et al. | 435/440 |
| 6,861,248 B1 | * | 3/2005 | Dale et al. | 435/255.2 |

* cited by examiner

*Primary Examiner*—Herbert J. Lilling

(57) ABSTRACT

A flocculent *Saccharomyces cerevisae* strain (BPSC-15) produces higher yields of ethanol in fermentations of fermentable sugar or fermentable starch/enzyme.

7 Claims, 6 Drawing Sheets

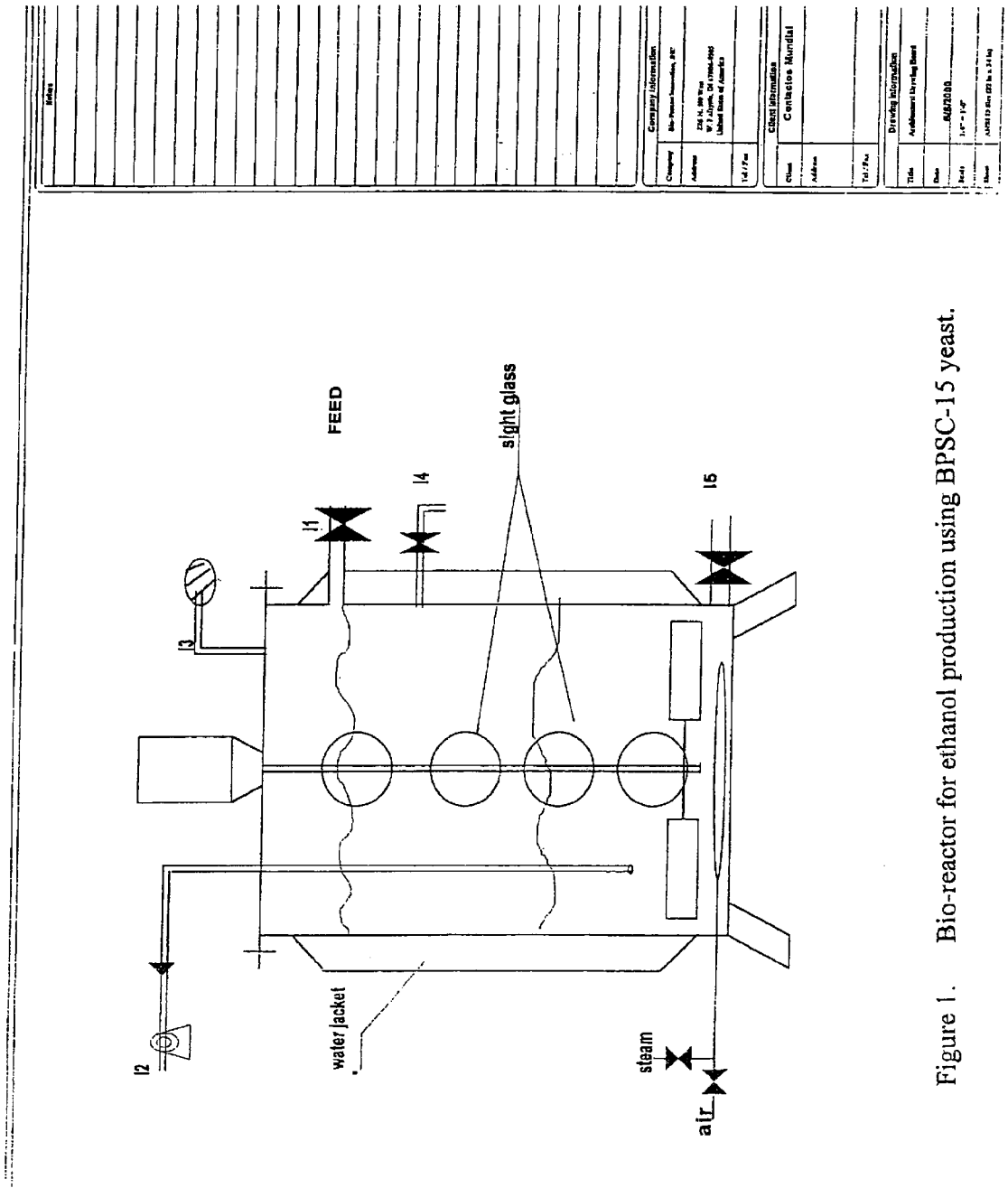
Figure 1. Bio-reactor for ethanol production using BPSC-15 yeast.

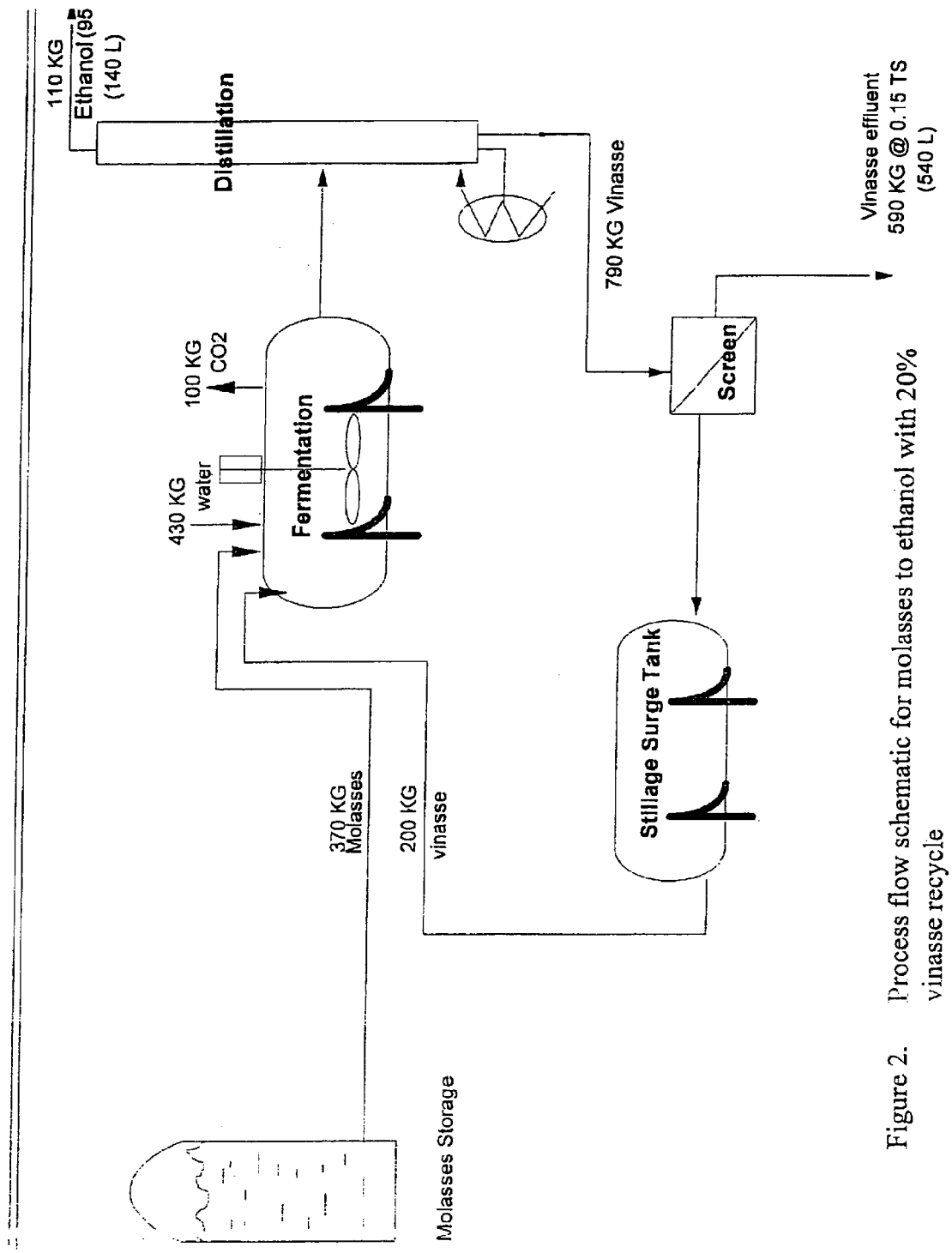
Figure 2. Process flow schematic for molasses to ethanol with 20% vinasse recycle

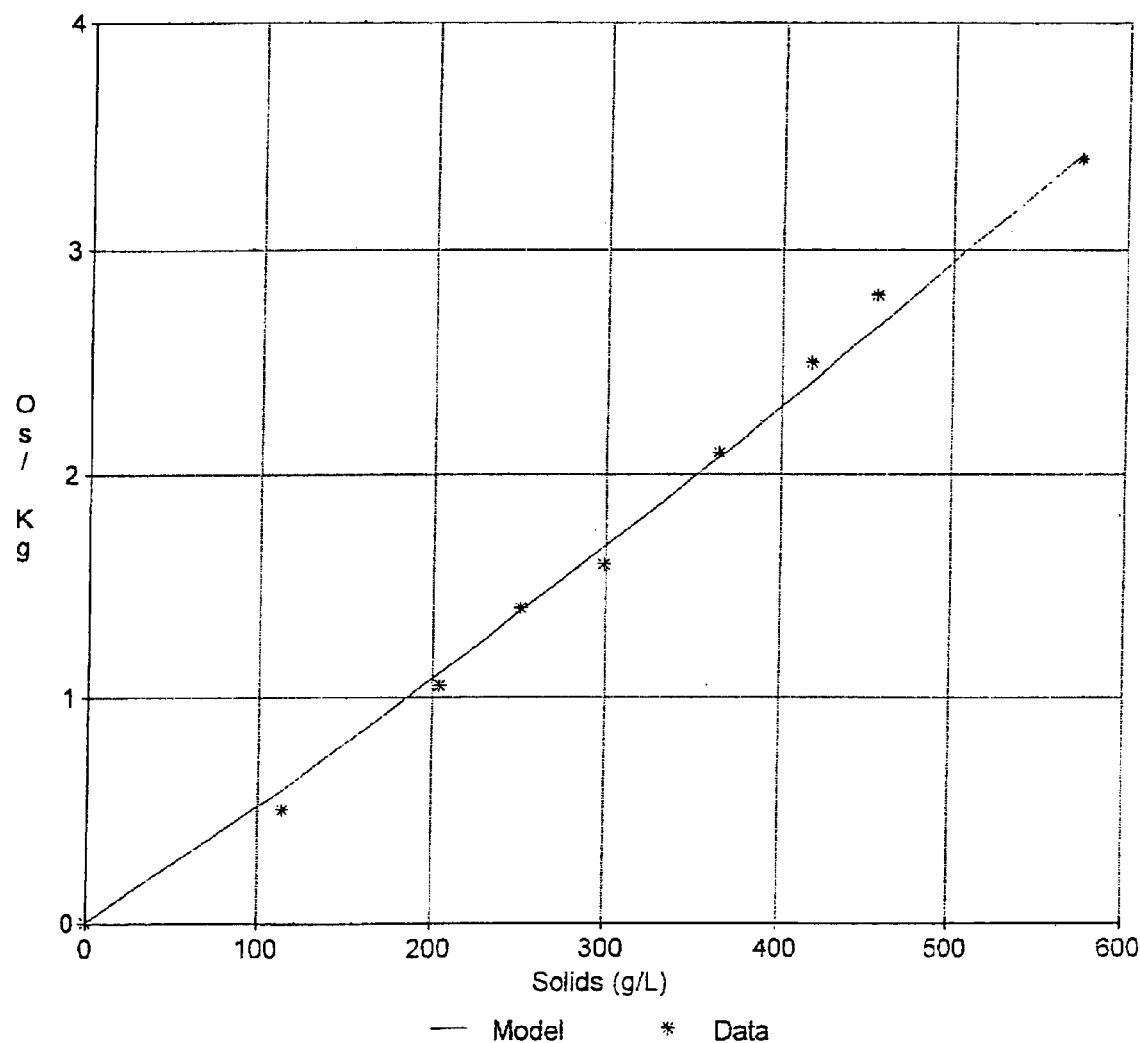
Figure 3. Osmolality of beet molasses as a function of molasses solids- model versus data.

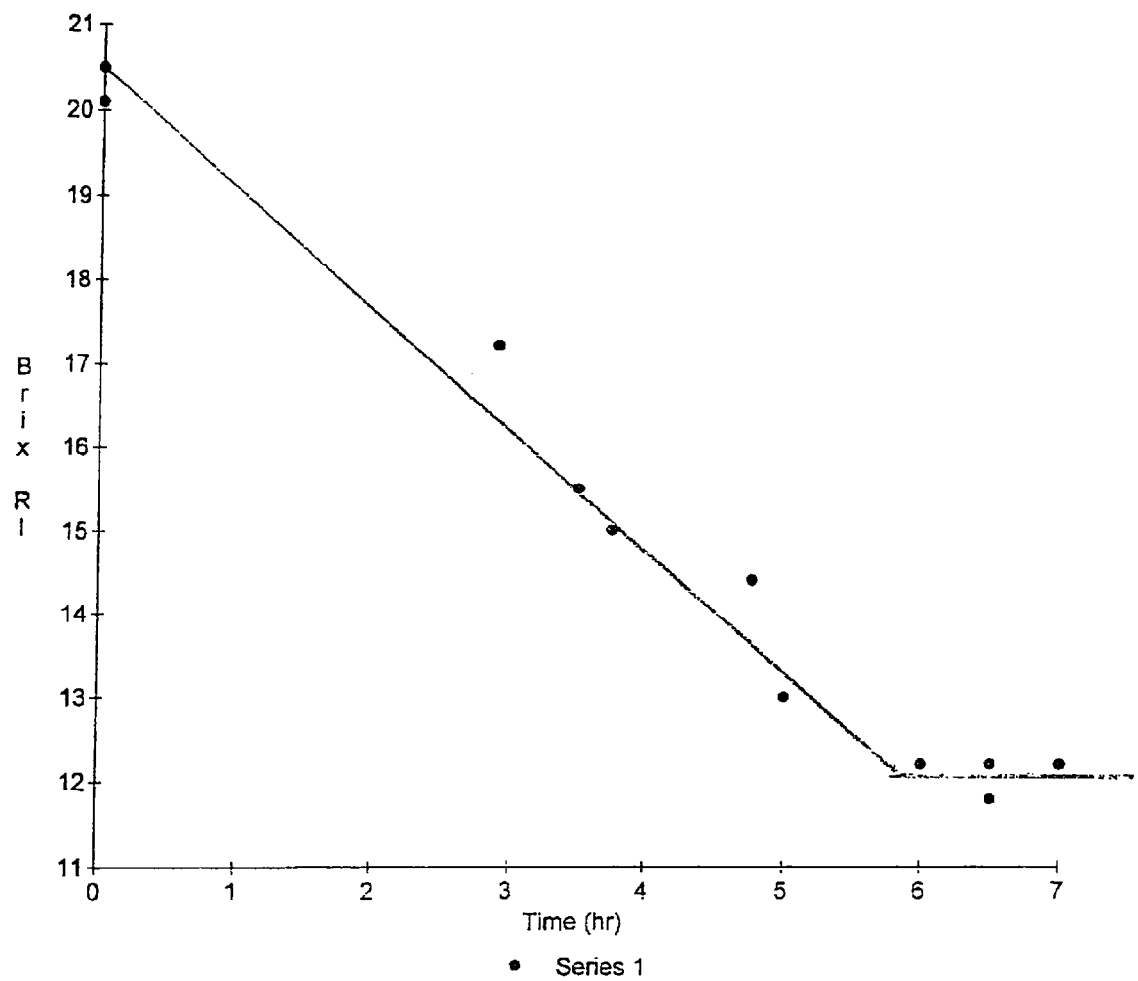
Figure 4. Consecutive Batch Mode (CBM) fermentation of beet molasses- data from 3 consecutive fermentations.

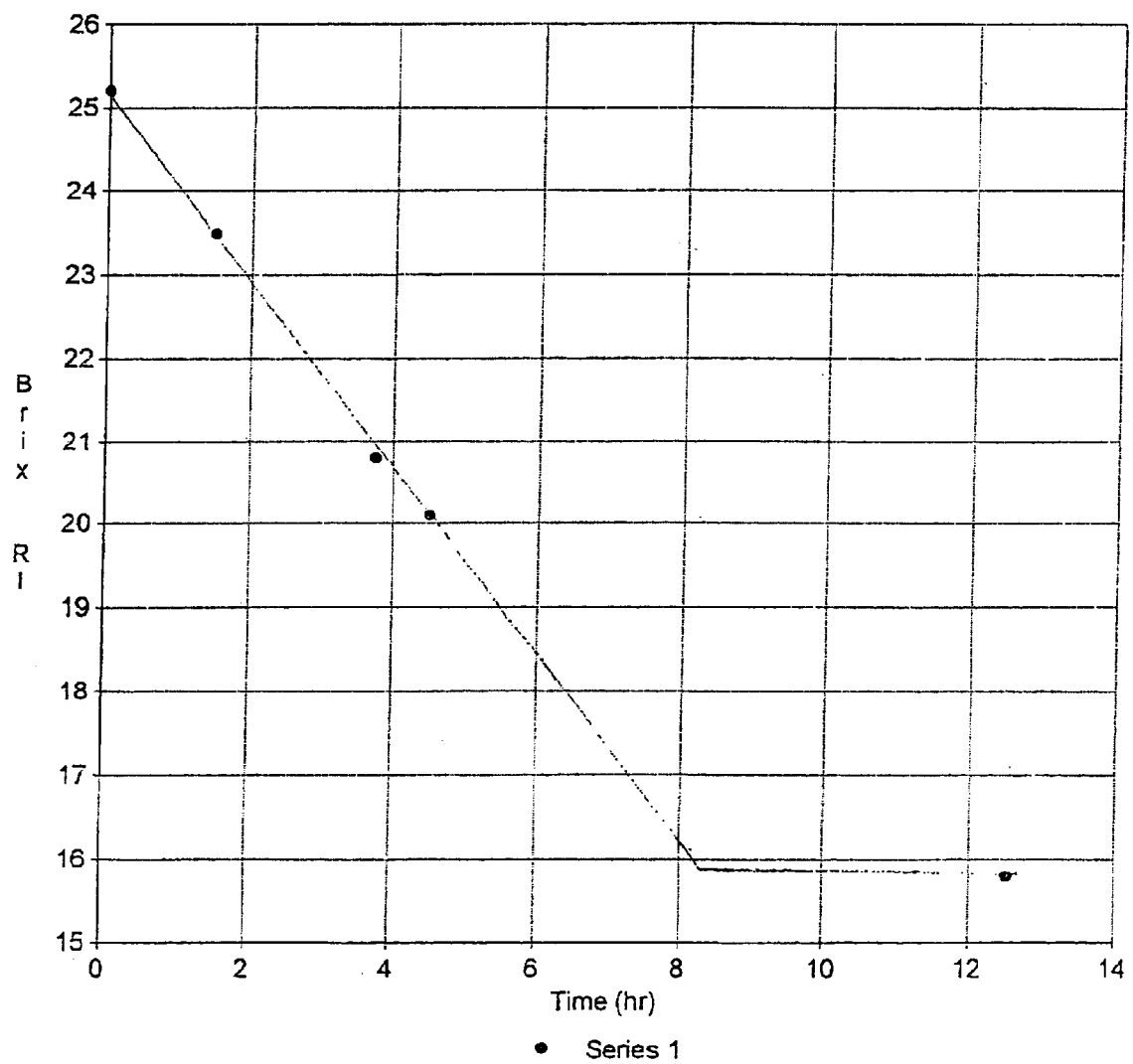
Figure 5. Consecutive Batch Mode (CBM) fermentation of beet molasses with 30% vinasse recycle.

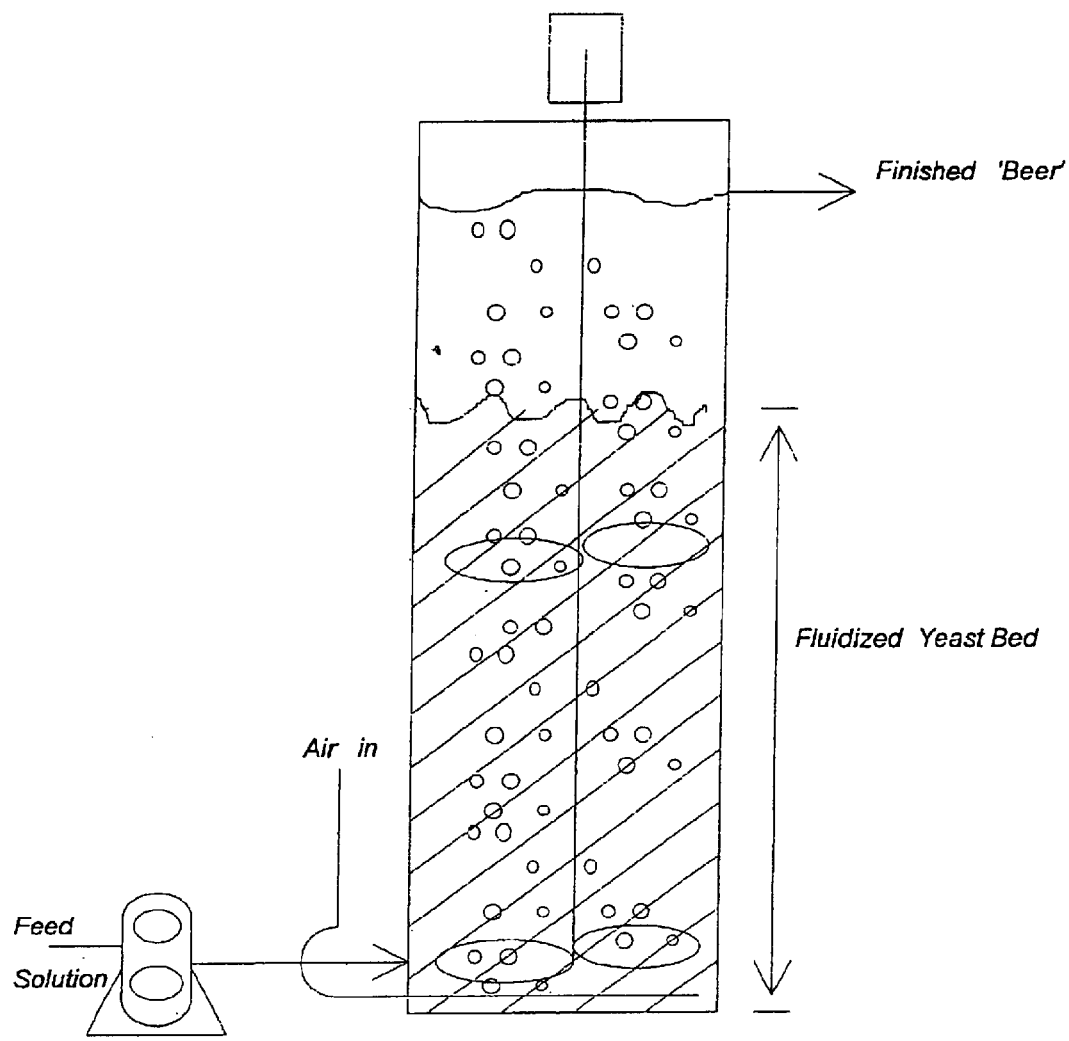
Figure 6.  Schematic of Tower Reactor with a fluidized yeast bed.

HIGH SPEED, CONSECUTIVE BATCH OR CONTINUOUS, LOW EFFLUENT PROCESS FOR THE PRODUCTION OF ETHANOL FROM MOLASSES, STARCHES, OR SUGARS

This is a continuation of application Ser. No. 10/056,063 filed Jan. 28, 2002, now U.S. Pat. No. 6,861,240 which claims the benefit of U.S. Provisional Application No. 60/264,070 filed Jan. 26, 2001. The entire disclosure of prior application Ser. No. 10/056,063 is hereby incorporated by reference.

FIELD OF THE INVENTION

A stable flocculating yeast strain developed by the inventors allows high yeast densities to be maintained in various bio-reactors, and is useful for performing high speed fermentations of sugars to ethanol and high speed, low-effluent fermentations (incorporating stillage recycle) for converting molasses, starch or fruit sugars to ethanol solutions.

BACKGROUND

The speed of fermentation of sugars to ethanol is a function of 1) yeast concentration, 2) basic composition of the fermentation media, and 3) levels of nutrients, pH and temperature. In general, fermentation rates increase linearly with increasing cell density.

$$F = X^* v(S, P, N, T) \quad \text{Eq.1}$$

where F is ethanol productivity as g ethanol produced per liter per hour,

X is g cells per liter, and v(S, P, N) is the specific ethanol production rate of ethanol (P), as a function of substrate (S), product concentration (P), nutrients (N), and temperature (T).

Dale et al (1994) showed that the inhibitory effects of high concentrations of 1) substrate, 2) product, and 3) salts can be linked to a single solution property, osmolality, which is basically the osmotic potential of the solution. Thus Equation 1 can be more accurately written as $$F = X^* v(O_{st}, N, T) \quad \text{Eq.2}$$

where $O_{st}$ is total solution osmolality which is in general an additive property of the osmolality of the various components in the media $$O_{st} = O_s(S) + O_s(P) + O_s(I) \quad \text{Eq.3}$$

where $O_s(S)$, $O_s(P)$, $O_s(I)$ are the osmolality due to the of the substrate (sugar, S), product (ethanol, E) and inerts/salts (I) in the media, respectively Dale et al, (1994) developed an osmolality describing both substrate and product inhibition of the ethanolic fermentation as:

$$v = v_m[1 - O_{st}/k_{vm}] \quad \text{Eq.4}$$

$$\mu = \mu_m[1 - O_{st}/k_{\mu m}] \quad \text{Eq.5}$$

Growth ($\mu$) is more strongly inhibited by osmolality than is productivity (v) with $k_{vm}$ values of ranging from around 2 to 2.5 os/kg, while $k_{vm}$ runs 3.5 to 5.0 depending upon yeast species, osmo-tolerance, and ethanol tolerance. Dale et al, 1994, show that for a standard *Saccharomyces* strain studied by Letourneau and Villa, 1987, that growth rates are totally inhibited at an osmolality of 1.9, while productivity is totally inhibited at 4.2. Equation 7 allows one to calculate the combined effects of sugars, ethanol, and salts on the fermentation rates. Cane and beet molasses are characterized by a high level of salts or minerals. The osmotic effect of these salts can be combined by lumping the salts as a single osmotic group forming 11% of the solids in an 80% molasses. The data are based on molasses osmolality by fitting the simple, lumped equation Eq. 3 with excellent results, as shown in FIG. 3. Using vinasse recycle reduces liquid effluent from the fermentation process, but causes the salts to build up in the fermentation broth, increasing solution osmolality, and inhibiting the fermentation rates as shown in Table 5. Thus, the ethanol producer must balance or optimize the benefits of reduced effluent waste water with the somewhat slower fermentation rates obtained.

Increasing temperature generally speeds a fermentation until the temperature becomes high enough to cause cell death. Fermentation rates are generally noted to increase from 20° to 32° C., doubling with a 5° C. increase in temperature.

There are two basic methods for accelerating the fermentation rates of a sugar media to ethanol, 1) increase the cell density, and/or 2) reduce the concentration of inhibitory compound(s) (with ethanol being most inhibitory due to its osmolality and toxic effects) in the media as suggested by Dale in prior U.S. Pat. Nos. 4,665,027 and 5,141,861. The focus of the invention described here is a method for maintaining a very high active cell density in the bio-reactor through the development and maintenance of a dense 'flocculated' yeast solid phase in the reactor. During a normal batch ethanol fermentation with standard *S. cerevisae* strains, a final cell concentration of between 1.5 and 15 g/l cells is achieved. It is often noted that cell growth completely stops after a certain cell density is reached (Holzberg et al, 1967). The oxygen tension in the fermentation is important in these batch fermentations, as the cells will convert a larger faction of the sugar substrate towards cell mass production as the amount of oxygen available to the cells increases. Trace oxygen can serve as a nutrient during the anaerobic fermentation of sugars, allowing the fermentation rate to increase with more cells produced. Cysewski and Wilke (1978) show an optimal oxygen tension of about 0.1 mm $O_2$. To maintain a cell density higher than the natural maximum attained in the fermenter, methods for keeping the cells in the fermenter must be utilized. A high cell density can be maintained either by recycling cells (through membrane or centrifugal techniques) or by retaining or immobilizing the cells within the reactor. Immobilization would seem to be advantageous as the capital expense of a cell recovery and recycle system can be eliminated. There has been a good deal of work over the last 10–15 years on immobilizing organisms to maintain a high cell density in the bioreactor. Immobilization can take one of several approaches, 1) entrapment within a gel bead or plate, 2) adsorption onto a solid matrix, or 3) self-agglomeration or flocculation into flakes or pellets.

Dale & Perrin, 1994, showed good performance of a yeast immobilized on a absorbent matrix. By incorporating simultaneous gas stripping of the ethanol product, we were able to ferment very concentrated molasses feed. Fermentation rates, F, of 12 to 65 g ethanol/L hr were noted on a liquid hold-up volume basis (about 4 to 21 g/L hr on a total reactor volume basis).

The use of flocculent yeast flakes or pellets to speed fermentation has been suggested by several researchers. Some yeasts have the property of joining together in clumps or flocs, with these multi-cell clumps having a much more rapid settling velocity than single cells. Flocculation is an important factor in the brewing process. After a potable beer or wine has completed its fermentation, it is desirable to have the yeast settle out. Standard *S. cerevisae* used for beer and wine fermentations is selected to have this post-fermentation flocculation characteristic. Standard wine or champagne yeasts settle over a period of 150 to 300 minutes if there is no fermentation activity to suspend the cells (Arikan and Ozilgen, 1992), while flocculent cells tend to settle so quickly it is difficult to get an OD on the cells as the cells settle in one minute in a cuvette (Castellon and Menawat, 1990). There is a body of literature on flocculation available with a review of the literature available (Calleja, 1989) and a number of papers discussing the effects of sugars (Kihn et al, 1988), ions [specifically sodium as a deflocculant (Castellon and Menawat, 1990) and calcium as a pro-flocculant (Kihn et al, 1988a; 1988b; and Masy et al, 1990)]. A microscopic study of flocculating fission yeast was reported by Sowden and Walker (1987, 1989) where a "hairy" or "mucilaginous" coating of the yeast is described. Soares et al, 1992, show that cell-cell interaction is important with a cell suspension of $2\times10^7$ cell/ml reaching a free cell density of $0.5\times10^6$ cell/ml in 2 minutes while a suspension starting at $1\times10^7$ cell/ml also settled to this same free cell density in 2 minutes. Faber et al (U.S. Pat. No. 4,567,145) describe a respiration deficient, flocculant strain of *S. uvarum* which, when settled externally to the reactor and then recycled to a single fermenter, could produce 5 to 7% ethanol at a fermentation rate of 50 g/L hr on a glucose feed.

Dale et al (1985) showed that, for an immobilized cell population exposed to constant conditions of ethanol and sugar, the steady state live cell fraction can be estimated based on a number of simplifying assumptions as:

$$X_{ssl}=[\mu/(\mu+K_d)] \qquad \text{Eq.6}$$

Where: $\mu$ is the specific growth rate of the cells ($hr^{-1}$), and $K_d$ is the death rate constant for the yeast ($hr^{-1}$) (where $K_d$ is a function of temperature, nutrient concentration, and toxic/inhibitory compound concentrations). Based on this analysis, we can see that if a cell population (i.e. the cells in one particular yeast pellet) is exposed to continuous conditions of zero growth, the steady state live cell density will be zero. Thus it is important for a pellet to occasionally see conditions allowing cell growth. There will be no probem for operation of reactor in the consecutive batch mode, as conditions at the beginning of the fermentation are conducive to growth (low ethanol, fresh nutrients). For the continuous cascade reactor, it is important that stage 1 conditions be maintained such that there is cell growth, with the overflow of these younger cells from stage one to stage two and subsequent stages refreshing the population of these stages where there will be little or no cell growth due to the higher solution osmolality (largely due to ethanol concentration).

The use of highly floccculent yeast for continuous reactors has been demonstrated by APV in a tower fermenter. Cell densities of 70–80 g/l were reported (Greenshield and Smith, 1970). Chen and Gong (1986) did further work on a flocculent tower type reactor. Cysewski and Wilke (1977) used a simple settler with cell recycle to attain high cell densities in a stirred reactor. However, no one has successfully applied a flocculent yeast fermentation to molasses, shown the stable long term performance obtained with our strain of yeast, or developed a minimal effluent process as described in this invention.

SUMMARY OF THE INVENTION

A process comprising 1) establishing a settled volume of between 5 and 80% (v/v) of a flocculent, pelletized yeast strain NRRL xx (internal designation # BPSC-15) in a stirred batch or continuous bio-reactor, 2) introducing a 10–40% by weight fermentable sugar medium (where the sugar(s) are, e.g., from a solution of molasses, high test molasses, converted starch/dextrin/glucose, or a fruit sugar) and further optionally containing from 0 to 90% (preferably from 20 to 70%) recycled stillage (this stillage is termed vinasse when from molasses), and 3) high speed (1 to 20 hour mean residence time) fermentation of the resulting medium to a 5 to 18% (w/v) ethanol 'beer' has been developed and demonstrated. Operating temperatures for all reactor types range from 5° to 45° C., preferably from 20° to 28° C. The pH of all reactor types is controlled at between 3.0 and 6.0, preferably at 4.0, by addition of any suitable base, preferably ammonia (either anhydrous or aqueous). Excellent resistance to bacterial contamination problems (i.e. lactic bacteria) is noted when fermentations are pH controlled at 4.0. Stirring is required in the reactor(s) to keep floc yeast from settling to the bottom and agglomerating into a solid mass. A gentle stirring action, combined with active generation of $CO_2$ yields excellent fermentations with BPSC-15; a stirring velocity giving a reactor Reynolds number between 3,000 and 25,000, preferably from 6,000 to 12,000, provides good performance of various reactor configurations. A pitched wide blade (blade diameter of from 50 to 90% of the reactor diameter), slow moving propeller—sweeping the bottom of the tank—is preferred over smaller, higher speed propellers (see FIG. 1).

The process is optionally operated in a Consecutive Batch Mode (CBM) consisting of charging the fermenter with a feed medium, starting stirring and optional micro-aeration (0.01 to 0.2 VVM—Volume of air per Volume of reactor per Minute—, preferably 0.05 VVM) in the reactor, and allowing fermentation to go to completion in a period ranging from 1 to 20 hours. The cells are then allowed to settle to the bottom of the fermenter by stopping stirring and aeration, where they form a 'solids' layer on the bottom of the reactor of between 1 and 80%, more especially from 5 and 60%, and preferably from 20 to 40%, of the reactor volume. The completed 'beer', consisting of the top liquid above the cell solids layer, is decanted. The reactor is then immediately ready for another fermentation cycle by simply charging with fresh medium. The basic design of a fermenter applicable for consecutive batch fermentations is shown in FIG. 1.

Alternatively, fresh feed is introduced continuously to one of two types of reactor, I) a tower reactor (TR), in which the yeast forms a 'fluidized bed' with a bed depth of from 5 to 95%, preferably from 60 to 80%) of the tower volume and the feed is introduced to the bottom of the TR. The completed beer is taken from the top of the reactor, which is operated with a residence time of from 0.25 to 20 hours, preferably from 2 to 4 hours. Alternatively, the feed is continuously added to II) a Continuous Multistage Reactor (CMR) where there is a series (2 to 10) of stirred reactors, connected by overflows from one to the next, with a floc cell density of between 5 and 100 g/L, preferably from 40 to 70 g/L, and completed beer overflows from the final reactor. Floc yeast pellets may need to be recycled from the effluent back to the first fermenter to maintain the yeast density on the stages. Residence time per stage can range from 0.25 to 8 hours, preferably from 1 to 3 hours.

Recycling of the stillage allows the process to be practiced in a low effluent mode. With molasses, stillage recycle of from 10 to 40%, preferably from 25 to 35%, is practical, reducing stillage production to from 3 to 6 liters per liter of 100% ethanol (versus 6.5 to 9 L stillage/vinasse with no stillage/vinasse recycle) with osmotic inhibition of fermentation rates increasing with increasing recycle rates due to build-up of salts in the fermentation medium. With starch/dextrins/glucose, the absence of salts allows recycle of from 50 to 90%, preferably from 60 to 80%, stillage during the make-up of fresh sugar solution feed, with resultant net effluent reduced to from 0.6 to 3 L stillage per liter ethanol.

BRIEF DESCRIPTION OF THE DRAWINGS

FIG. 1. Bio-reactor for ethanol production using BPSC-15 yeast.

FIG. 2. Process flow schematic for molasses to ethanol with 20% vinasse recycle.

FIG. 3. Osmolality of beet molasses as a function of molasses solids—model versus data.

FIG. 4. Consecutive Batch Mode (CBM) fermentation of beet molasses—data from 3 consecutive fermentations.

FIG. 5. Consecutive Batch Mode (CBM) fermentation of beet molasses with 30% vinasse recycle.

FIG. 6. Schematic of Tower Reactor with a fluidized yeast bed.

DETAILS

A flocculent, *Saccharomyces cerevisae* strain, BPSC-15, is deposited with USDA NRRL culture collection as NRRL Y-xx. Under the conditions described herein, this yeast forms small, disc shaped pellets which are maintained in suspension by stirring. This yeast yields (when given a clear feed) a final beer which is still clear [less than 0.5 g/L free cells (where free cells are defined as single and single budding yeast)] with yeast pellets which settle more or less instantaneously (settling velocity of from 1 to 4 cm/s) when stirring ceases.

The process of developing the strain began with acquiring and testing flocculating ethanolic strains from various culture collections. A long process of selecting, adapting, and re-selecting a mutant strain, using the criteria of floc stability and osmo-tolerance, starting with the highly flocculent parent strain *S. cerevisae* ATCC 60593. The adaptation/mutation process comprised the following steps:

1) first selecting for floc stability by running a continuous single stage CSTR for a period of weeks, selecting a 'best' pellet, using this pellet as a starting inoculation for a second CSTR, and repeating this process until a stable well shaped floc cell mass was able to maintain excellent performance over a period of 3 months;

2) secondly, using the stable floc mutant parent strain developed in step one and improving its osmo-tolerance by repeatedly growing and transferring a small 'pellet' of floc yeast in a 15 ml selective media in a test tube (i.e. a high salt media), taking a single pellet from this tube and growing it again in a test tube with fresh selective media [20 g/L NaCl, 100 g/L glucose, 3 g/L each of Yeast extract, Malt extract and Peptone (YMP)]. This process was repeated every 10 to 14 days for a period of several months (10 transfers);

3) finally, this new, stable, osmo-tolerant mutant strain of *Saccharomyces cerevisae* was maintained in a refrigerated 50 ml test tube w/10 ml of high salt (50 g/L NaCl, 50 g/L glucose YMP) for period ranging between 2 and 4 months after transferring (growing from a small transferred pellet for 100 hours at 25° to 30° C.

The new biologically pure yeast strain, BPSC-15, is easily distinguished from its parent strain by 1) showing growth and fermentation while maintaining a totally floc mode [i.e. a free cell density of less than 0.5 g/L (approximately $2 \times 10^7$ cell per ml) while floc density can exceed 100 g/L] in a variety of media as described herein, including unclarified molasses, and 2) has a final osmo-tolerance for ethanol productivity ($k_{vm}$ from Eq. 7) of 5.0 os/kg versus 3.8 for the parent strain.

The yeast is grown-up from a pellet maintained in a refrigerated test tube as above, and a small pellet is transferred using a wire loop (using sterile techniques) to an aerated (0.2 to 2.0 VVM aeration rate) 100 to 500 ml flask filled 20% with sterile growth medium (20 g/L glucose, 3 g/L each of yeast extract, malt extract and peptone). The flask is then incubated at from 20° to 25° C. for from 24 to 60 hours. Upon completion of growth, the cells appear as a flaky white 'snow' of small pellets (less than 1 mm) in this aerated medium. The supernatant medium is decanted, and settled cells added to a bio-reactor fitted with 1) aeration, 2) cooling—a jacket, coils, or external heat exchanger—and 3) low speed stirring, as per FIG. 1, for implementation of the process in the Consecutive Batch Mode (CBM). The cell mass in terms of settled cell density is initially developed in 3 to 4 repeated fermentations using 'growth conditions' [higher aeration rates (0.1 to 1.0 VVM), higher levels of nutrients, and lower levels of sugars—from 6 to 12% w/v]. After a settled cell volume of 10 to 15% of the total reactor volume is obtained (after a 1 to 10 minute settling time), the reactor is optionally moved to high speed/low effluent fermentation mode as per the flow diagram of FIG. 2 where the feed to the reactor is a mix of water, feed substrate, and recycled stillage (vinasse). Air is introduced into the reactor through an air sparger (such as a sintered glass air stone or other bubbling device) at a rate of between zero and 0.20 VVM (volume air per volume reactor per minute), and stirring of the reactor is adjusted so as to lift the cells gently from the bottom of the reactor. In a highly turbulent reactor operation, the cells can be deflocculated. Also the size of the floc pellet grows smaller as turbulence in the reactor increases. Under standard minimal stirring speeds (125 RPM) and an aeration rate of zero to 0.2 VVM (Volume air per Volume fermenter per Minute) with fermentation in a 2L MultiGen bioreactor, flocs form small cylindrical disks with a diameter of from 1 to 2 mm and a thickness of perhaps 0.5 mm. The settling rates of the 1 to 2 mm floc disks are from 2.1 cm/s to 3.2 cm/s in 20° C. tap water. Thus, even in a commercial scale (15 to 20 ft depth reactor) all the flocs are expected to have settled within 3 to 5 minutes (assuming quiescence in the reactor).

Basic Procedures and Parameters for Growth of Inoculation Culture and Initiation of High Speed Fermentation w/BPSC-15

The strain is stored and maintained in refrigerated 50 ml capped sterile liquid media test tubes filled with 10 ml of maintenance medium as described previously. To begin a fermentation using BPSC-15, a 150 ml flask is filled to about 50% (75 ml) of growth medium as given in Table 1. The flask and medium are sterilized by autoclaving at 15 psig steam pressure for 30 minutes. It is to be understood that there is a wide variety of nutritional formulations using both complex and defined media which will give the yeast the required carbohydrate, protein, vitamins, and minerals required for fast growth other than the media compositions suggested below. The nutritional needs for BPSC-15 are no different than standard baker's or distiller's yeast which are well known and documented in the yeast production industry (see for example Wegner, U.S. Pat. No. 4,414,329, and Plomp, U.S. Pat. No. 5,916,609).

TABLE 1

Growth Medium

| Component | Range | Preferred |
|---|---|---|
| Carbohydrate: glucose or sucrose | 2–200 g/L | 20 g/L |
| Complex Nutrients | | |
| Yeast Extract | 0–20 g/L | 3 g/L |
| Malt Extract | 0–20 g/L | 3 g/L |
| Peptone | 0–20 g/L | 3 g/L |
| pH | 3.0–6.0 | 4.0–5.0 |

To initiate growth, a small pellet, culture loop, or several ml of cell culure are transferred from the culture tube (using sterile techniques) to 150 to 300 ml of an aerated growth media (Table 1) in a 500 ml flask which is then incubated either on a rotary shaker at from 30 to 350 RPM, preferably 120 RPM, or aerated using an air stone or other bubbling device connected to a sterile air source at from 0.1 to 2.0, preferably 1, VVM (Volume air per Volume reactor per Minute). The aerated flask can be stirred with a magnetic stir bar at from 0 to 300 RPM, preferably 120 RPM. The temperature of the flask is maintained at from 15° to 35° C., preferably 25° C., for a period of time ranging between 12 and 60 hours depending upon temperature, size of the inoculation, activity of the inoculation, etc. The media will be observed to get cloudy with free cells, and then for the cells to agglomerate into small pellets, similar to the snow seen in liquid filled paper weights. These cells are optionally 1) reset if more cells are desired, simply by pouring off the media from the settled cells, and then filling back up with fresh growth media, 2) used to start a small scale fermentation, or 3) used to inoculate a larger aerated growth tank when commercial scale quantities of starter yeast are desired. A larger aerated growth tank of 25 to 100 L is fitted with a stirrer stirring at from 0 to 200 RPM, preferably 30 RPM. The aeration itself will give fairly good agitation in the reactor. If more cells are desired than are grown in a single cycle, the cells can be allowed to settle, the supernatant (exhausted growth media) decanted, and more sterile growth medium added to the flask or growth vessel. This cycling is optionally repeated several times to build-up the volume of settled yeast in the flask if desired.

To begin a fermentation with BPSC-15, the settled cells from aerobic growth are transferred to a fermentation medium. The fermentation medium can be molasses, sucrose, fructose or glucose based. Table 2 shows possible media and nutritional supplements.

TABLE 2

Fermentation Medium

| Component | Range | Preferred |
|---|---|---|
| Carbohydrate: glucose, sucrose fructose or molasses | 20–400 g/L | 250 g/L |
| Complex Nutrients (YMP) | | |
| Yeast Extract | 0–20 g/L | 2 g/L |
| Malt Extract | 0–20 g/L | 2 g/L |
| Peptone | 0–20 g/L | 2 g/L |
| Complex Nutrients (Steep) | | |
| Corn Steep Liquor | 1–50 g/L | 10 g/L |
| Ammonium sulfate | 0.5–15 | 5 g/L |
| Potassium phosphate | 0.1–5 | 1.5 g/L |
| Micro-nutrients* | | |
| pH | 3.0–6.0 | 4.0 |

*includes biotin, niacin, pantothenic acid, and trace minerals

In developing this yeast, 'richer' media, i.e. the levels given in Table 2 as preferred levels, are considered good cell growth, with the settled cell volume increasing by from 10 to 50% per cycle in consecutive batch fermentations (where completed 'beer' is decanted and the settled cells retained in the reactor). As with the growth media, there are many formulations which will meet the yeasts' needs for carbohydrate, protein/nitrogen, vitamins and minerals. It is also possible to operate the reactor (once the desired yeast layer depth is achieved) with reduced levels of nutrients, once there is no further need to produce yeast. Reducing the nutrient levels reduces costs for the media as well as improves the ethanol yield (g ethanol per g sugar utilized), as less sugar is used for cell growth. There are enough nutrients available in molasses (either cane or beet) to support an active fermentation once the desired level of yeast is attained.

The innoculum to the fermentation media can be from 0.1 to 30%, preferably from 5 to 10%, of the volume of the fermentation media. The fermentation vessel should incorporate 1) stirring (5 to 400 RPM, preferably 30 to 150 RPM) where a reactor Reynolds number (Eq.7) of from 3,000 to 12,000 is generally adequate to lift and mix the settled cell floc layer, 2) temperature control at 15° to 38° C., preferably 28° C., 3) aeration (0 to 0.5 VVM, preferably 0.05 VVM), and pH control with the pH controlled at between 3.0 and 6.0, preferably at 4.0. pH is controlled by a pH controller which adds acid or base to hold the pH at the desired pH. Generally the fermentation produces a low level of acid by-products, causing the pH to drop. pH is thus controlled by adding base, such as sodium hydroxide, calcium oxide or hydroxide or any such liquid or solid base, or, preferably, anhydrous ammonia or aqeous ammonium hydroxide. Ammonia serves both as a pH control agent and a nutrient for the yeast fermentation.

The inoculation is effected in a sterile fashion to the fermentation vessel, and stirring, aeration (if used) and pH control commenced. The yeast begins fermenting, producing $CO_2$ and ethanol from the sugar(s). The fermentation is finished in from 12 to 80 hours depending upon the size and activity of the inoculation. Once the fermentation is complete [as determined by either complete utilization of the sugar(s) or no further $CO_2$ evolution/ethanol production], stirring is stopped, the cell flocs/pellets allowed to settle, and the beer decanted from the fermenter while leaving the cell layer in the bottom of the reactor. (The beer can be decanted from the cells by draining the reactor either from the side, or from an effluent pipeline dropped from the top of the reactor to a point off the bottom of the reactor.)

A second—consecutive—fermentation is then started by refilling the reactor with fresh fermentation media (as per Table 2) to the initial reactor volume. Stirring and aeration are re-commenced, and the fermentation allowed to go to completion. This process is then repeated as often as desired with the settled yeast bed allowed to grow to a desired level between 2 and 70%, preferably from 25 to 35%, of the operating fermenter volume. At this point the fermentation is usually completed in a period of from 1 to 8 hours.

After a settled cell volume of 10 to 15% of the total reactor volume is obtained (after a 1 to 10 minute settling time for the yeast floc), the reactor is optionally moved to a high speed/low effluent fermentation mode as per the flow diagram of FIG. 2 where the feed to the reactor is a mix of water, feed substrate, and recycled stillage (vinasse). Air is introduced to the reactor through an air sparger. The stirring of the reactor is adjusted so as to lift the cells gently from the bottom of the reactor. In highly turbulent reactor operation, the cells can be deflocculated. Also, the size of the floc pellet grows smaller as turbulence in the reactor increases. Under standard minimal stirring speeds (e.g. 125 RPM) and an aeration rate of from zero to 0.2 VVM conditions in a 2L MultiGen bioreactor, the flocs form small cylindrical disks with a diameter of from 1 to 2 mm and a thickness of perhaps 0.5 mm. The settling rates of the 1 to 2 mm floc disks is observed at 2.1 cm/s to 3.2 cm/s in 20° C. tap water. Thus, even in a commercial scale (e.g. a 15 to 20 ft depth reactor) all of the flocs are expected to settle within 3 to 5 minutes (assuming quiescence in the reactor).

EXAMPLE 1

High Speed Consecutive Batch Mode (CBM) with Molasses Substrate

Long Term Floc Stability—Fresh fermentation broth consisting of 200 ml of molasses in a 500 ml flask at an initial brix of 27° (as measured by refractive index) is inoculated with a 20 ml inoculum of aerobically grown yeast (BPSC-15) pellets. The reactor is stirred at 100 RPM with a magnetic stirrer and held at 25° C. in a temperature controlled incubator. No pH control is needed due to the buffering capacity of the molasses. This fermentation is near completion in 70 hours at a final brix of 19°, with 86 g/L ethanol measured along with some unfermented sugars using HPLC. The yeast is allowed to settle, the supernatant 'beer' broth is poured off, and the flask refilled with 180 ml of fresh medium, initial brix 25.5°. A brix of 18.2° is noted at 20 hours with an ethanol concentration of 83.5 g/L. This procedure is repeated daily for 30 days, for a total of 36 repeated fermentations. Average settled cell volume reaches from 60 to 80 ml (15 to 45 minutes settling time), and ethanol concentrations range from 85 to 110 g/L with little to no residual sugars. Ethanol, sucrose, and fermentation by products are measured by HPLC (high pressure liquid chromatography) using an Aminex carbohydrate column. During settling time, the cell mass becomes more compact or compresses over time, with from 100 to 120 ml of cells settling by 4 minutes after stirring and after aeration is stopped, the cell mass further compressing to about 65 ml at 45 minutes. This CBM experiment is finally terminated with no reason to believe that it could not be continued indefinitely.

High Speed Fermentation—A set of experiments is performed using a 2L Multigen reactor which is fitted with temperature control and a 6 bladed 4 cm speed controlled mag drive turbine for mixing. The minimum propeller speed to lift the cell pellets corresponds to from 100 to 150 RPM. At 100 RPM, pellets begin settling in some portions of the reactor. These propeller speeds correspond to a reactor Reynolds number of 4,300 (100 RPM) and 5,450 (125 RPM) where the Reynolds number for a stirred tank is defined as:

$$Re = \frac{D_p^2 * N * \rho}{\mu_l} \qquad Eq.\ 7$$

where $D_p$ is the propeller diameter
N is the propeller speed (Rev per second)
$\rho$ is the density of the liquid
$\mu_l$ is the viscosity of the liquid The brix (as measured by Refractive Index or RI) as a function of time is shown in FIG. 4 for three different consecutive batch fermentations. As per FIG. 4, the reaction goes to completion in a little over 6 hours with data taken from different fermentations being essentially co-linear. Final ethanol concentration of fermentation (at 12.0° brix final RI) is measured at 103 g/L (13.1% v/v).

Scale-Up—The High Speed CBM trials are repeated on a 100 L scale using the reactor shown in FIG. 1 with cane molasses as a feed. Essentially identical performance to 2L reactor trials is obtained as shown in Table 3. With a 100 L pilot plant a stirring velocity of 3 to 4 RPM is found sufficient to lift the flocs [Reynolds (stirrer) of 8,000 to 11,000].

TABLE 3

Performance of 100 L Pilot Plant with Molasses and BPSC-15 Yeast

| Trial #1 | Initial Brix | Final Brix | Op. Temp | Time of Ferm | Vol % Yeast |
|---|---|---|---|---|---|
| 1 | 15° | 7° | 80° F. | 6 hr | 8 |
| 2 | 15° | 8° | 82° | 6 hr | 8.5 |
| 3 | 15° | 8° | 80° | 7 hr | 9 |
| 4 | 15° | 9° | 82° | 75 hr | 10 |

EXAMPLE 2

High Speed Continuous Multistage Reactor (CMR) with Molasses

The expected performance of a 3-stage continuous reactor system with beet molasses is modeled by a mass balance on each of the main components in the fermentation broth, cells (X), sugar (S), and ethanol (P). Each of these components affect the rate of cell fermentation, growth, and consequent cell concentration in the reactor stage. When the concentration of cells leaving the reactor is the same as the concentration of cells within the reactor, which is generally the case, an analysis for a single stage reactor (with no input cells) at steady state simply indicates that growth rate must equal the dilution rate. If, as Dale et al (1994) proposed, $\mu$ (specific cell growth rate—g cell/g cell/hr) and $v$ (specific productivity—g ethanol/g cell/hr) are largely a function of osmolality, then a certain dilution rate will correspond to a certain solution osmolality at which cell growth will equal dilution rate. However, if highly flocculent cells are present, the cell density in the overflow can be substantially less than the steady state concentration in the reactor.

When a model of a 3 stage cascade reactor system is written in BASIC, the mass balances on the stages are written as:

$$P_{ss(n)} = P_{ss(n-1)} + X_{ss(\mu)} * \tau * v \qquad Eq.\ 8$$

$$S_{ss(n)} = S_{ss(n-1)} - \Delta P_{(n)}/Y_{p/s} \qquad Eq.\ 9$$

where $X_{ss(n)}$ is the steady state concentration of cells (g/L) on stage n, $P_{ss(n)}$ and $S_{ss(n)}$ are the concentrations of ethanol and sugar (g/L) on stage n, and $\tau$ is the residence time on the stage (volume of reactor divided by the feed rate per hour).

$v$ is written as a function of osmolality, dependent on the sum of osmolality of: 1) inert salt (I), 2) ethanol (P) and 3) sugar—sucrose (S) on the stage as per Equations 3 and 4. Osmolality for a molasses solution was modeled as:

$$O_{st} = O_s(S) + O_s(P) + O_s(I) \qquad Eq.\ 10$$

where $O_s(S) = (0.004 * S)^{1.2}$; $O_s(P) = (0.022 * P)^{1.1}$; $O_s(I) = (0.023 * I)$ Osmolality for molasses using this model is compared to osmolality data for molasses in FIG. 5. Osmolality in the fermentation broth as a function of reaction completion ($\epsilon$) for a batch fermentation of molasses is shown in Table 4 along with the calculated specific relative ethanol productivity ($v/v_{max}$) of the floc yeast BPSC-15.

TABLE 4

Model for Fermentation of Molasses

| $\epsilon$ | Sugar (g/L) | Ethanol | Salts | Osmol | v/v |
|---|---|---|---|---|---|
| 0.00 | 240 | 0 | 48 | 2.06 | 0.64 |
| 0.10 | 216 | 11.2 | 48 | 2.16 | 0.61 |
| 0.20 | 192 | 22.4 | 48 | 2.29 | 0.58 |
| 0.30 | 168 | 33.6 | 48 | 2.44 | 0.55 |
| 0.40 | 144 | 44.8 | 48 | 2.60 | 0.51 |
| 0.50 | 120 | 56 | 48 | 2.78 | 0.47 |
| 0.60 | 96 | 67.2 | 48 | 2.96 | 0.43 |
| 0.70 | 72 | 78.4 | 48 | 3.15 | 0.38 |
| 0.80 | 48 | 89.6 | 48 | 3.35 | 0.34 |
| 0.90 | 24 | 100.8 | 48 | 3.57 | 0.29 |
| 1.00 | 0 | 112 | 48 | 3.80 | 0.00 |

As sucrose is converted to ethanol, the osmolality (as indicated by Table 4) of the fermentation broth increases. In the example above, beginning with a molasses fermentation with 350 g/L solids, the initial sugar concentration is 240 g/L, and the initial salt concentration is 48 g/L. Osmolality is initially 2.06 os/kg, and rises to 3.8 os/kg as the sugar is converted to ethanol with a final ethanol concentration of 112 g/L in this example. Relative specific productivity of the cells falls from 64% of $v_{max}$ to 29% as the fermentation nears completion. Finally, with no sugar, final fermentation rates are zero. We determined a maximal osmolality ($k_{vm}$) for BPSC-15 as 5.0 os/kg based on a measured value of 135 g/L ethanol in a concentrated molasses fermentation medium.

This system of equations (Eq. 8, 9, & 10) can be solved iteratively to find steady state concentrations ethanol and sugar in a multistage continuous reactor system. With flocculent cells, a steady state cell density of 20% settled volume corresponds to about 40 g/L dry cells. The model determines steady state sugar and ethanol concentrations along with the final osmolality on the stage. The outlet ethanol increases as the residence time per stage increases. The predicted ethanol, sucrose and osmolatiy concentration on each of the stages of a 3 stage continuous cascade reactor is shown in Table 5 for two systems, one with a feed of 240 g/L fermentable sugar and a residence time of 3 hours per stage, and a second example with a feed of 220 g/L sugar and a residence time of 2.5 hours per stage.

TABLE 5

Model of 3 Stage Continuous Reactor with Molasses Substrate

| XSi | Cells (g/L) | t (hr) | KOS (os/kg) | OSi |
|---|---|---|---|---|
| 240 | 40 | 3 | 4.3 | 2.250431 |

| | S (g/L) | P (g/L) | Osmol (os/kg) |
|---|---|---|---|
| Stage 1 | 127.9 | 53.3 | 2.9 |
| Stage 2 | 53.4 | 88.9 | 3.5 |
| Stage 3 | 14.7 | 107.3 | 3.9 |

| XSi | Cells (g/L) | t (hr) | KOS | OSi |
|---|---|---|---|---|
| 220 | 40 | 2.5 | 4.3 | 2.047384 |

TABLE 5-continued

Model of 3 Stage Continuous Reactor with Molasses Substrate

| | S (g/L) | P (g/L) | Osmol (os/kg) |
|---|---|---|---|
| Stage 1 | 117.1 | 49.0 | 2.6 |
| Stage 2 | 47.5 | 82.1 | 3.2 |
| Stage 3 | 13.2 | 98.5 | 3.6 |

Based on the values for $K_{os}$ there is an asymptotic approach to approximately 135 g/l outlet ethanol as residence times are increased, which is the limit imposed by the osmolality of the salts plus the ethanol in a molasses finished fermentation medium.

In operating a 3 stage continuous reactor system on molasses, performance is very close to the performance modeled in Table 5, as shown in Table 6 when operating with a residence time of 3.4 hours/stage. It is necessary to return yeast flocs from the effluent to the first stage due to the high rate of fermentation activity in the reactor and the consequent high amount of $CO_2$ evolution. The floccs leave the reactor with the overflow.

TABLE 6

Performance of 3 stage Cascade CSTR w/BPSC-15

| | BRIX (RI) | Eth. (g/L) |
|---|---|---|
| Feed Brix | 24 | 0 |
| Stage 1 | 21.7 | 49.7 |
| Stage 2 | 18.5 | not meas |
| Stage 3 | 16.5 | 106 |
| t per stg | 3.4 | hours |

EXAMPLE 4

Lab Scale Performance of BPSC-15 Yeast with Corn Syrup in Continuous Cascade Mode of Operation BPI's High Speed/Low Effluent system on corn syrup, as well in the continuous cascade mode, is tested. A 1 liter Multigen reactor is used. Batches of 5 gallons feed are made-up to run the 3 experiments described in Table 5. The reactor effluent is caught in a closed stainless steel vessel held at 65° C. to kill the yeast and prevent further fermentation of the effluent. The effluent is then transferred to the feed tanks to simulate stage 2, and once again to simulate stage 3. The volume of dead cells in the bottom of the effluent pot is measured after each stage, and the dry wt. estimated. A nutrient formulation comprising inorganic N, P and K supplemented with micro-nutrients/vitamins and some 'Nutri-ferm', a type of corn steep liquor, from Pekin Energy Inc., is used, as also shown in Table 2.

The results from these experiments are shown in the table below. The trials started with a 3 hour residence time. Near complete sugar utilization is noted in two stages (6 hours total) although there is still measurable glucose noted (4 g/L). Cutting the residence time to 2 hours/stg, 6 hours total, stage 3 has only 30 g/L glucose in the feed, which is reduced to an unmeasurable (under 0.5 g/L) level. Reducing the residence time again to 1.3 hours per stage (4 hours total), should feed about 50 g/L glucose to Stage 3 based on a modeling of the system, instead a 77 g/L glucose/68 g/L ethanol feed to stage 3 propduces 97 g/L ethanol, 13 g/L glucose as a final product.

Some problems are encountered with temperature control (overheating) in Stage 1, which causes Stage 2 to perform less well than it should have at the 1.3 hour RTD. Performance of stage 2 improves over time after improving the cooling system, with a final sample of the overflow showing glucose reduced to 55 g/L versus an average of 77 g/L.

TABLE 7

BPI HS/LE Fermentation of Corn Syrup

|  | time (RTD) Hr | Ethanol g/L | Sugar g/L | Productivity g eth/L hr | g cells/L out |
|---|---|---|---|---|---|
| Feed | 3 hour/stg |  | 220 |  |  |
| Stg 1 | 3 | 73 | 57 | 24.3 | m.m. |
| Stg 2 | 6 | 105 | 4 | 10.7 | m.m. |
| Feed | 2 hour/stg |  | 230 |  |  |
| Stg 1 | 2 | 63.6 | 98 | 31.8 | 1.1 |
| Stg 2 | 4 | 95 | 30 | 15.7 | 0.4 |
| Stg 3 | 6 | 110 | 0.2 | 7.5 | 0.4 |
| Feed | 1.3 hour/stg |  | 210 |  |  |
| Stg 1 | 1.33 | 40 | 128 | 30.1 | 1 |
| Stg 2 | 2.66 | 68 | 77 | 21.1 | 0.7 |
| Stg 3 | 4 | 97 | 13 | 21.8 | 0.4 |

Basically, a productivity of around 30 grams ethanol per L hr for stage 1 is noted when the ethanol level in the reactor is under 65 g/L. Productivity of stages 2 and 3 range from 10 to 22 g/L depending on sugar availability and ethanol concentrations. The system run at 4 hour total RTD gives 12 to 13% ethanol (v/v) with very low residual sugars.

EXAMPLE 5

High Speed Fermentation of Grain/Starch/Glucose and Fruit Sugars in a Tower Reactor (TR)

The use of BPSC-15 yeast in a tower reactor is demonstrated over extended periods of time. A tower reactor [where a tower reactor is characterized by a Height to Diameter (H/D) ratio of 3 to 10] is constructed as show in FIG. 6 with a total active volume of 500 ml. Feed substrate and air are introduced to the bottom of the reactor. The reactor is fitted with a magnetic stirrer to spread the feed and air evenly across the bottom of the reactor; The $CO_2$ evolved from the rapid fermentation of the substrate causes the yeast pellets to form a 'fluidized bed' characterized by an active movement of the pellets as the $CO_2$ and air move through the bed of pellets to the top of the reactor.

This reactor operated continuously over a period of several months. Fermentation of a glucose/malt extract feed of 11 brix goes to completion (50 g/L ethanol) in a residence time of approximately two hours (feed rate of 250 ml/hr). There is a steady state 'fluidized bed' depth of approximately 60 to 90% of the reactor volume. When the feed is stopped, the yeast bed depth slowly compresses to from 30 to 45% of the reactor volume. A feed of 20° brix grape juice (fructose sugar) fed to the reactor for a period of several weeks resulted in 90 g/L ethanol 'wine' obtained in a residence time of 4 hours.

EXAMPLE 6

Low Effluent Production from Beet or Cane Molasses Fermentation in CBM—The Effects of Vinasse Recycle Waste water production from the fermentation of molasses has the potential of a major disposal problem for companies producing ethanol from molasses. If a 7% by volume concentration of ethanol (55 g/L) is produced in a batch fermentation, there will be approximately 13 liters of stillage, termed vinasse, per each liter of 200 proof ethanol recovered from the distillation. One can try to minimize waste water by 1) producing higher concentrations of ethanol, and 2) recycling the vinasse when making up fresh molasses fermentation broth. With the process of this invention, either CBM, TR, or CMM, ethanol concentrations of 13 to 15% v/v (up to 125 g/L) are reached within a 6 to 9 hour fermentation. This higher ethanol concentration reduces the vinasse production to only 6 to 7 liters vinasse per liter ethanol. Recycling vinasse when making up fresh media further reduces effluent volume, although there is an inhibitory effect due to recycling of salts. The effect of recycle on effluent vinasse salt concentration for a molasses feed of 350 g/L fresh molasses solids (220 g/L sugars, 44 g/L salt) is shown in Table 8 using Eq. 8 and 9 along with a mass balance on the reactor with vinasse recycle as shown in FIG. 2.

TABLE 8

Calculated Effect of Vinasse Recycle on Effluent Volume and Fermentation Broth Osmolality

| % Vinasse Recycle | Vinasse Salts (g/L) | Liter Vinas per L Eth | Inital Broth Osm | Final Broth Osm | v/v Avg Ferm F |
|---|---|---|---|---|---|
| 0 | 52.4 | 6.5 | 1.87 | 3.52 | 0.49 |
| 10 | 59.5 | 5.7 | 2.01 | 3.66 | 0.46 |
| 15 | 63.8 | 5.3 | 2.09 | 3.74 | 0.44 |
| 20 | 68.8 | 4.9 | 2.19 | 3.84 | 0.42 |
| 25 | 74.6 | 4.5 | 2.30 | 3.95 | 0.39 |
| 30 | 81.5 | 4.2 | 2.43 | 4.09 | 0.36 |
| 35 | 89.8 | 3.8 | 2.59 | 4.25 | 0.32 |
| 40 | 100.0 | 3.4 | 2.79 | 4.44 | 0.28 |

As per this table, effluent volume decreases from 6.5 L vinasse/stillage with no recycle, to 3.4 L vinasse per liter of ethanol product at 40% recycle. Maximum osmolality at which ethanol is produced by BPSC-15 is about 4.8 os/kg. For recycle of rates of 40% or higher, final broth osmolality approaches this limit. Recycling at 20% reduces average fermentation rates by about 20%, while recycling at 30% causes a 35% decrease in the average fermentation rates during batch fermentation. At 40% recycle, the fermentation finishes slowly with the fermentation rate inhibited by over 90% as the reaction nears completion due to the osmolality approaching 4.8. In general, 20 to 25% recycling reduces effluent from 23 to 31% while reducing average fermentation rates only 25%. The effects of using 10, 20 and 30% vinasse recycle in the fermentation media were determined. Quick and complete fermentations are realized in from 7 to 10 hours. FIG. 5 shows a sample fermentation performance from the fermentation of molasses with 30% backset in the 2L Multigen fermenter.

In conclusion, recycling 20 to 30% vinasse/stillage in making up the fermentation broth along with the high levels of ethanol which floc yeast can produce allows the process to reduce effluent volume from 13 L vinasse/stillage per liter of ethanol product (as is currently the case in some batch operations on molasses yielding 55 g/L ethanol), to only 4 to 5 L vinasse per liter ethanol while still allowing a 7 to 9 hour high speed fermentation reaching 100 g/L ethanol concentration. If 40% vinasse is recycled, effluent can be reduced to 3.4 L per L of ethanol product.

EXAMPLE 7

High Speed/Low Effluent Fermentation of Starch/ Dextrins/Glucose, 'High Test Molasses' and Fruit Sugars This process also applies to the fermentation of any 'clear' fermentation medium, such as liquefied starch (dextrins)— as that resulting from a wet mill corn processing plant or any other source of starch (potatoes, wheat, barley etc.) It applies as well to fruit syrups as from apples, grapes, pears, or other fruit pressings. It applies to cane and beet press juice and their concentrates (termed 'high test molasses') with excellent results due to the lower level of salts in these streams. It does not, however, apply to a 'dry mill corn mash' containing a high amount of insoluble corn fiber and hulls, as the flocs could not be easily separated from these solids. The process does, however, work for a dry mill corn system when the insoluble corn solids are removed via filtering or centrifugation, as suggested by Zinnamosca et al (U.S. Pat. No. 5,545,543) prior to fermentation.

The fermentation of starch dextrin is most efficiently completed when the dextrin is converted to glucose while the fermentation is in progress (Simultaneous Saccharification and Fermentation). This allows initial osmolality to be lower, and consequently yields higher initial fermentation rates. For example, assuming that the average dextrin has a chain length of 6 glucose units after a jet cook liquefaction of a starch stream, a 30% solids solution would have an osmolality of 0.43 as compared to 2.58 for a fully converted 30% glucose solution. An initial osmolality of 2.58 in the glucose solution would cause specific yeast fermentation rates to be reduced by 50% from maximal rates ($v_{max}$). Due to the lack of salts, higher levels of ethanol are reached with starch as compared to molasses. With no stillage recycle, final ethanol concentrations of 175 g/L or 21% by volume are attained. When a final fermentation rate of 15% of $v_{max}$ is set (so as to allow the fermentation to complete in a reasonable time frame), a final osmolality of 4.15 or 150 g/L ethanol is attained with no other contributing osmotic inhibitors. Instead of salts, by-product glycerol build-up or other non fermentables keep recycling of stillage to 90% or less. Glycerol is produced as aminor by-product of the yeast fermentation at a rate of about 0.02 to 0.04 g glycerol per g sugar fermented. Using a glycerol production value (Y p/s) of 0.03, the concentration of glycerol in the exit stillage increases as the degree of recycle of the stillage to the fermentation broth increases as shown in Table 6. Given a feed of 220 g/L starch, with no stillage recycle, the effluent has 8.9 g/L glycerol, which increases to 44.8 g/L as 80% of the stillage is brought back. The effects of increasing the degree of stillage recycle on alycerol and other non-fermentables (i.e. non-converted starch, salts, etc) are shown in Table 9.

TABLE 9

Low Effluent Fermentation of Starch/Fruit Sugars Effects of Recycle on Glycerol and Non-fermentables Conc.

| % Stillage Recycle to Feed | Glycerol Conc | Non-Fermentabl Conc. Factor | Vol Effluen per L ethar |
|---|---|---|---|
| 0 | 8.9 g/L | 1X | 5.7 L |
| 50 | 17.9 g/L | 2X | 2.8 |
| 60 | 22.4 g/L | 2.5X | 2.3 |
| 70 | 30 g/L | 3.4X | 1.7 |
| 80 | 44.8 g/L | 5X | 1.1 |
| 90 | 89.5 | 10X | 0.56 |

The high density pelletized yeast process described herein useful in a variety of reactor configurations, with the advantage of speeding the reaction due to the maintenance of a high active cell density in the reactor without a need for centrifuges, cell washing, membrane separation, or similar cell recycle systems sometimes practiced in the industry. The two types of continuous reactors presented here, the Tower Reactor (TR), and the Multistage Continuous Mode (CBR) reactor alternatively can be operated in series. Other applications include reaction with simultaneous ethanol separation as suggested by Dale (U.S. Pat. Nos. 4,665,027 and 5,141,861) with gas stripping of ethanol from the broth, the vacu-ferm fermention suggested by Ramalingam and Finn (1977), the coupled fermentation/distillation Biostil process developed by Alpha Laval and then acquired by Chematur Engineering (1994), etc.

The high density pelletized flocculant yeast process is also applicable to potable beers, wines, and grain alcohols for distilled beverages, as well as industrial and fuel alcohol from fruit sugars, cane press juice (high test molasses), corn/grain based starches/sugars, celllulose hydrolysate or any source of glucose, sucrose, maltose or fructose sugars.

The strength and durability of the flocc pellet are negatively influenced by the presence of high levels of insoluble solids in the media. When added to a viscous whole corn mash, no yeast pellets are noted after the fermentation is completed. In repeated experiments with strained corn mash (the mash strained through a 40 mesh sieve after saccharification) a loss of pellet strength and settling rate is noted due to the presence of insoluble corn solids which passed through the sieve.

The reactor is very resistant to bacterial infection, but a high load of bacteria can cause the performance of the reactor(s) to deteriorate. Care must be exercised to ensure that wild yeast and bacteria are not introduced to the reactor. Although the reactor is resistant to many types of contamination, performance and flavor can be degraded through contaminating organisms.

The invention and its advantages are readily understood from the foregoing description. It is apparent that various changes can be made in the process and compositions without departing from the spirit and scope of the invention or sacrificing its material advantages. The processes and compositions hereinbefore described are merely illustrative of preferred embodiments of the invention.

BIBLIOGRAPHY

Arikan, O and M. Ozilgen. 1992. Settling Kinetics of Champagne Yeast. Ens. Mic. Tech. 14:762

Chen, C., M. C. Dale and M. R. Okos. 1990. "The Long Term Effects of Ethanol on Immobilized Cell Reactor Performance." Biotechnology and Bioengineering. 36:975

Chen, L. F. and C. S. Gong. 1986. Continuous Ethanol Production using Induced Yeast Aggregates. App. Micro. Biotech 25:208

Chematur Engineering Inc. 1994. Introduction to Biostil. Promotional Corporate Literature from Chematur Engineering.

Cysewski, G. and C. Wilke. 1978. Process Design and Economics for Alternative Fermenation Methods. Biot. Bioeng. 20:1421.

Dale, M. C., U.S. Pat. No. 4,665,027. 1987. An Immobilized cell Reactor with Simultaneous Separation and Methods for Design and Use Thereof. Co-inventors: M. R. Okos, P. C. Wankat.

Dale, M. C. U.S. Pat. No. 5,141,861. 1992. Method of Use of a Multi-Stage Reactor with Simultaneous Separation.

Dale, M. C., A. Eagger, and M. R. Okos. 1994. "Osmolality Effects on Free and Immobilized K. fragilis Growth and Productivity in Whey Permeate Concentrate." Process Biochemistry. 29:535–544

Dale, M. C., N. Perrin, and M. Okos. 1994. "Production of Ethanol from Concentrated Sucrose and Molasses Solution Using *S. Pombe* in an Immobilized Cell Reactor Separator." AICHE Symposium Series #300 Vol 90:56–62.

Dale, M. C., C. Chen and M. R. Okos. 1990. "The Effects of Ethanol and Temperature on Immobilized Cell Reactors: Cell Growth and Death Rates as Critical Factors in Reactor Modeling and Design." Biotechnology and Bioengineering. 36:983

Dale, M. C., C. Chen, and M. Okos. 1990. The Effects of Ethanol and Temperature on Immobilized Cell Reactor Performance. Biot. Bioeng. 36:983.

Dale, M. C., M. R. Okos and P. C. Wankat, 1985. "An Immobilized Cell Reactor with Simultaneous Product Separation: I. Reactor Design and Analysis." Biotechnology and Bioengineering. 27:932.

Faber, M., J. Bernstein, and M. Grossman. 1986. Continuous production of ethanol by use of respiration deficient mutant yeast. U.S. Pat. No. 4,567,145.

Greenshields R. and E. Smith. 1971. A tower fermenter w/flocculent yeast. Chem. Eng. 249:182

Holzberg, I, R. Finn, and K. Steinkraus. 1967. A Kinetic Study of the Alcoholic Fermentation of Grape Juice. Biotech Bioeng. 9:413.

Jarzeuski, A., J. Malinowski, and G. Goma. 1989. Modeling of Ethanol Fermentation at High Yeast Concentrations. Biot. Bioeng. 34.1225

Johnson, B. L. Sowden and T. Walker. 1989. Use of electron microscopy to characterize the surfaces of flocculent and non-flocculent yeast. Can. J. Micro 35:1081

Kihn, J., C. Masy and M. Mestdagh. 1988. Yeast Flocculation: nonspecific repulsion and specific bonding. Can J Micro 34:773.

Kihn, J. C. Masy, M. Mastdagh, and P. Rouxhet. 1988. Yeast Flocculation: Factors affecting the measurement of flocculence. Can J Micro 34:779

Lin, J., M. C. Dale, and M. Okos. 1991. "Osmotic ($a_w$) Effects on Growth and Ethanol Production of Free and Immobilized *Z. mobilis*." Process Biochem. 26:143.

Masy, C. M. Kockerols and M. Mastdagh. 1991. Calcium activity as a key factor in the induction of flocculation in industrial fermentations. Can J Micro 37:295

Ramalingham, A. and R. K. Finn. 1977. Ethanol Production via a Vacuum Fermentation. Biot. Bioeng. 19,583

Soares, E. J. Teixiera, and M. Mota, 1992. Interaction between flocculent and nonflocculent cells of *S. cerevisae*. Can. J. Micro. 38:969

Soares, E. J. Teixiera, and M. Mota, 1991. Influence of aeration and glucose concentration in the flocculation of *S. cerevisae*. Biot. Lett. 13:207

Sowden, L. and T. Walker. 1988. Electron microscopy of flocullating yeast. Can J. Micro 34:577

Taylor, N., and W. Orton. 1975. Temperature Effects on Flocculation of Yeasts. J. Inst. Brew. London 81:53.

Teixeira J. and M. Mota. 1990. Experimental Assessment of Internal Diffusion Limitations in Yeast Flocs. Chem Eng. J. 43:13

Zinnamosca, F. and M. Berruti. Process for the continuous production of ethanol from cereals. U.S. Pat. No. 5,545,543

What is claimed is:

1. A method of developing an improved strain of *Saccharomyces cerevisae* which comprises a) a selecting a highly flocculent strain of that species, b) running a continuous single stage CSTR for a period of weeks, c) selecting, based on floc stability, a 'best' pellet, d) using this pellet as a starting inoculation for running a second CSTR, e) repeating steps b), c) and d) until an obtained stable well shaped floc cell mass is capable of maintaining consistent performance over a period of time, f) improving the osmo-tolerance of the stable floc mutant obtained from step d) by growing a small pellet thereof in a high-salt medium, g) taking a single pellet from the resulting medium and growing it again in fresh medium, h) repeating steps f) and g) a number of times until a new, highly flocculent, stable, osmo-tolerant mutant strain of *Saccharomyces cerevisae* is obtained.

2. A method of claim 1 wherein the highly flocculent strain of step a) is *S. cerevisae* ATCC 60593.

3. A biologically pure culture of a *Saccharomyces cerevisae* strain which i) has the capability to maintain a totally floc mode characterized by yeast pellets of from 0.1 to 5 mm in diameter in a fermentation medium, ii) shows a yeast free cell (single or budding double cells) of less than 0.5 g/L with a yeast floc density as high as 100 g/L or higher, iii) has a limiting osmo-tolerance for ethanol productivity of about 5.0 os/kg, and iv) is substantially the same as an improved strain obtained by the method of claim 2.

4. A method of claim 1 wherein the mutant strain obtained from step h) i) has the capability to maintain a totally floc mode characterized by yeast pellets of from 0.1 to 5 mm in diameter in a fermentation medium, ii) shows a yeast free cell (single or budding double cells) of less than 0.5 g/L with a yeast floc density as high as 100 g/L or higher, and iii) has a limiting osmo-tolerance for ethanol productivity of about 5.0 os/kg.

5. A method of claim 4 which further comprises producing an ethanol 'beer' solution in a bioreactor at a pH of between 3.0 and 8.0 and a temperature between 5° and 45° C., from a fermentation medium comprised of a fermentable carbohydrate, optional recycle stillage, requisite nutrients and an effective amount of the obtained mutant strain of *Saccharomyces cerevisae*.

6. A biologically pure culture of a *Saccharomyces cerevisae* strain which i) has the capability to maintain a totally floc mode characterized by yeast pellets of from 0.1 to 5 mm in diameter in a fermentation medium, ii) shows a yeast free cell (single or budding double cells) of less than 0.5 g/L with a yeast floc density as high as 100 g/L or higher, iii) has a limiting osmo-tolerance for ethanol productivity of about 5.0 os/kg, and iv) is substantially the same as an improved strain obtained by the method of claim 1.

7. A biologically pure culture of a *Saccharomyces cerevisae* strain which i) has the capability to maintain a totally floc mode characterized by yeast pellets of from 0.1 to 5 mm in diameter in a fermentation medium, ii) shows a yeast free cell (single or budding double cells) of less than 0.5 g/L with a yeast floc density as high as 100 g/L or higher, and iii) has a limiting osmo-tolerance for ethanol productivity of about 5.0 os/kg.

* * * * *